(12) United States Patent
Protopsaltis

(10) Patent No.: US 8,968,192 B2
(45) Date of Patent: Mar. 3, 2015

(54) SYSTEMS AND METHODS FOR TISSUE RETRACTION

(75) Inventor: Dimitri K. Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1544 days.

(21) Appl. No.: 12/134,318

(22) Filed: Jun. 6, 2008

(65) Prior Publication Data
US 2009/0306480 A1    Dec. 10, 2009

(51) Int. Cl.
  *A61B 1/32*      (2006.01)
  *A61B 17/02*     (2006.01)
  *A61B 17/00*     (2006.01)

(52) U.S. Cl.
  CPC ......... *A61B 17/0206* (2013.01); *A61B 17/0293* (2013.01); *A61B 2017/00539* (2013.01)
  USPC ...................................................... 600/219

(58) Field of Classification Search
  USPC ......... 600/201, 202, 207, 215, 219, 222, 224, 600/229, 230, 233, 184, 228, 231; 606/90, 606/192, 57; 604/104, 107, 191, 198; 254/50.3, 201, 228, 423; 73/857
  See application file for complete search history.

(56) References Cited

U.S. PATENT DOCUMENTS

| | | | |
|---|---|---|---|
| 563,236 A | 7/1896 | Penhall | |
| 1,400,616 A | 12/1921 | McCrory | |
| 1,613,141 A | 1/1927 | Stein | |
| 2,073,510 A * | 3/1937 | Bishman | 254/50.3 |
| 2,661,735 A | 7/1952 | Davis | |
| 2,670,731 A | 3/1954 | Zoll | |
| 2,693,795 A | 11/1954 | Grieshaber | |
| 3,054,398 A | 9/1962 | Kobler | |
| 3,747,592 A | 7/1973 | Santos | |
| 3,752,149 A | 8/1973 | Ungar | |
| 3,788,318 A | 1/1974 | Kim | |
| 3,965,890 A | 6/1976 | Gauthier | |
| 4,024,860 A * | 5/1977 | Chelnokov et al. | 602/32 |
| 4,263,899 A | 4/1981 | Burgin | |
| 4,380,999 A | 4/1983 | Healy | |
| 4,501,266 A * | 2/1985 | McDaniel | 606/90 |
| 4,545,374 A | 10/1985 | Jacobson | |
| 4,616,635 A | 10/1986 | Caspar | |

(Continued)

FOREIGN PATENT DOCUMENTS

| | | |
|---|---|---|
| DE | 4028651 | 3/1992 |
| EP | 0336526 | 10/1989 |

(Continued)

*Primary Examiner* — Christian Sevilla
(74) *Attorney, Agent, or Firm* — Sorell, Lenna & Schmidt, LLP

(57) ABSTRACT

A retractor system for percutaneous surgery in a patient includes first and second retractor portions positionable opposite one another in an incision of the patient. An actuating member is coupled with and extends between ends of the retractor portions which are positionable above the incision. The actuating member is in communication with a controller which includes a user interface for receiving actuation commands from the user. In response to actuation commands, the actuating member is actuated and its length is adjusted to position the first and second retractor portions relative to one another in the incision. In another form, a method is directed to retracting tissue for percutaneous access to a surgical site in a patient. However, other embodiments, forms and applications are also envisioned.

15 Claims, 6 Drawing Sheets

(56) References Cited

U.S. PATENT DOCUMENTS

| | | |
|---|---|---|
| 4,716,901 A | 1/1988 | Jackson |
| 4,747,394 A | 5/1988 | Watanabe |
| 4,747,395 A | 5/1988 | Brief |
| 4,765,311 A | 8/1988 | Kulik |
| 4,817,587 A | 4/1989 | Janese |
| 4,852,552 A | 8/1989 | Chaux |
| 4,862,891 A | 9/1989 | Smith |
| 4,899,729 A | 2/1990 | Gill |
| 4,924,857 A * | 5/1990 | Mahmoodian ............... 600/220 |
| 5,027,793 A | 7/1991 | Engelhardt |
| 5,052,373 A | 10/1991 | Michelson |
| 5,125,396 A | 6/1992 | Ray |
| 5,139,511 A | 8/1992 | Gill |
| 5,158,545 A | 10/1992 | Trudell |
| 5,163,949 A | 11/1992 | Bonutti |
| 5,197,971 A | 3/1993 | Bonutti |
| 5,271,384 A * | 12/1993 | McEwen et al. ............. 600/201 |
| 5,299,563 A | 4/1994 | Seton |
| 5,312,417 A | 5/1994 | Wilk |
| 5,339,803 A | 8/1994 | Mayzels |
| 5,353,784 A | 10/1994 | Nady-Mohamed |
| 5,389,080 A | 2/1995 | Yoon |
| 5,490,819 A | 2/1996 | Nicholas |
| 5,503,617 A | 4/1996 | Jako |
| 5,509,893 A | 4/1996 | Pracas |
| 5,512,038 A | 4/1996 | O'Neal |
| 5,549,595 A | 8/1996 | Freitas |
| 5,573,517 A | 11/1996 | Bonutti |
| 5,618,260 A | 4/1997 | Caspar |
| 5,667,481 A | 9/1997 | Villalta |
| 5,674,240 A | 10/1997 | Bonutti |
| 5,681,265 A | 10/1997 | Maeda |
| 5,688,223 A | 11/1997 | Rosendahl |
| 5,707,359 A | 1/1998 | Bufalini |
| 5,728,046 A | 3/1998 | Mayer |
| 5,755,732 A | 5/1998 | Green |
| 5,776,054 A | 7/1998 | Bobra |
| 5,779,629 A | 7/1998 | Hohlen |
| 5,786,648 A | 7/1998 | Iwanami |
| 5,795,291 A | 8/1998 | Koros |
| 5,813,978 A | 9/1998 | Jako |
| 5,823,947 A | 10/1998 | Yoon |
| 5,865,731 A | 2/1999 | Lenox |
| 5,888,196 A | 3/1999 | Bonutti |
| 5,928,139 A | 7/1999 | Koros |
| 5,931,777 A | 8/1999 | Sava |
| 5,944,658 A | 8/1999 | Koros |
| 5,951,466 A | 9/1999 | Segermark |
| 5,961,499 A | 10/1999 | Bonutti |
| 5,976,146 A | 11/1999 | Ogawa |
| 6,027,518 A | 2/2000 | Gaber |
| 6,042,540 A | 3/2000 | Johnston |
| 6,074,343 A | 6/2000 | Nathanson |
| 6,074,380 A | 6/2000 | Byrne |
| 6,083,154 A | 7/2000 | Liu |
| 6,096,046 A | 8/2000 | Weiss |
| 6,099,547 A | 8/2000 | Gellman |
| 6,139,493 A | 10/2000 | Koros |
| 6,149,583 A | 11/2000 | Vierra |
| 6,162,236 A | 12/2000 | Osada |
| 6,171,299 B1 | 1/2001 | Bonutti |
| 6,187,000 B1 | 2/2001 | Davison |
| 6,196,969 B1 | 3/2001 | Bester |
| 6,200,322 B1 | 3/2001 | Branch |
| 6,224,545 B1 | 5/2001 | Cocchia |
| 6,296,609 B1 | 10/2001 | Brau |
| 6,312,443 B1 | 11/2001 | Stone |
| 6,325,812 B1 | 12/2001 | Dubrul |
| 6,361,492 B1 | 3/2002 | Santilli |
| 6,371,911 B1 | 4/2002 | Hossain |
| 6,378,671 B1 | 4/2002 | Carlson |
| 6,394,950 B1 | 5/2002 | Weiss |
| 6,423,069 B1 * | 7/2002 | Sellers ............................ 606/71 |
| 6,431,025 B1 | 8/2002 | Koros |
| 6,450,952 B1 | 9/2002 | Rioux |
| 6,565,576 B1 * | 5/2003 | Stauch et al. ................. 606/105 |
| 6,602,189 B1 | 8/2003 | Bennetti |
| 6,616,605 B2 | 9/2003 | Wright |
| 6,781,284 B1 | 8/2004 | Pelrine |
| 6,918,910 B2 * | 7/2005 | Smith et al. .................... 606/60 |
| 6,945,933 B2 | 9/2005 | Branch |
| 7,008,377 B2 | 3/2006 | Beane |
| 7,288,075 B2 | 10/2007 | Parihar |
| 7,615,055 B2 * | 11/2009 | DiSilvestro .................... 606/88 |
| 7,686,813 B2 * | 3/2010 | Stutz et al. ..................... 606/90 |
| 8,162,944 B2 * | 4/2012 | Cohen et al. ................... 606/71 |
| 8,177,789 B2 * | 5/2012 | Magill et al. ................. 606/105 |
| 2003/0055319 A1 | 3/2003 | Chang |
| 2004/0002629 A1 | 1/2004 | Branch |
| 2004/0176665 A1 | 9/2004 | Branch |
| 2004/0230191 A1 | 11/2004 | Frey |
| 2005/0021034 A1 * | 1/2005 | Cohen et al. ................... 606/71 |
| 2005/0113644 A1 | 5/2005 | Obenchain |
| 2005/0192485 A1 | 9/2005 | Branch |
| 2005/0234304 A1 | 10/2005 | Dewey |
| 2006/0037467 A1 * | 2/2006 | McCarroll et al. ............. 91/361 |
| 2006/0069315 A1 | 3/2006 | Miles |
| 2006/0271096 A1 * | 11/2006 | Hamada ....................... 606/198 |

FOREIGN PATENT DOCUMENTS

| | | |
|---|---|---|
| EP | 0856286 | 8/1998 |
| EP | 0951868 | 10/1999 |
| EP | 1053717 | 11/2000 |
| EP | 1192905 | 4/2002 |
| FR | 2788958 | 8/2000 |
| FR | 2807313 | 10/2001 |
| WO | WO 2005/030318 A1 | 4/2005 |

* cited by examiner

SYSTEMS AND METHODS FOR TISSUE RETRACTION

BACKGROUND

The present application relates to systems and methods for performing tissue retraction to facilitate a procedure, such as minimally invasive surgery, within in a patient.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

SUMMARY

One nonlimiting embodiment of the present application is directed to a retractor system for percutaneous surgery in a patient that includes first and second retractor portions positionable opposite one another in an incision of the patient. The retractor portions include a proximal end positionable above the incision and to which an actuating member is coupled. Upon actuation, the length of the actuating member is adjustable to position the first and second retractor portions relative to one another. The retractor system also includes a controller in communication with the actuating member. A user interface is provided on the controller for receiving actuation commands from the user. The actuating member is operable to respond to the actuation commands to position the retractor portions relative to each other. However, in other embodiments, different forms and applications are envisioned.

Another embodiment of the present application is a unique system for percutaneous surgery in a patient. Other embodiments include unique methods, systems, devices, kits, assemblies, equipment, and/or apparatus involving a retractor.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
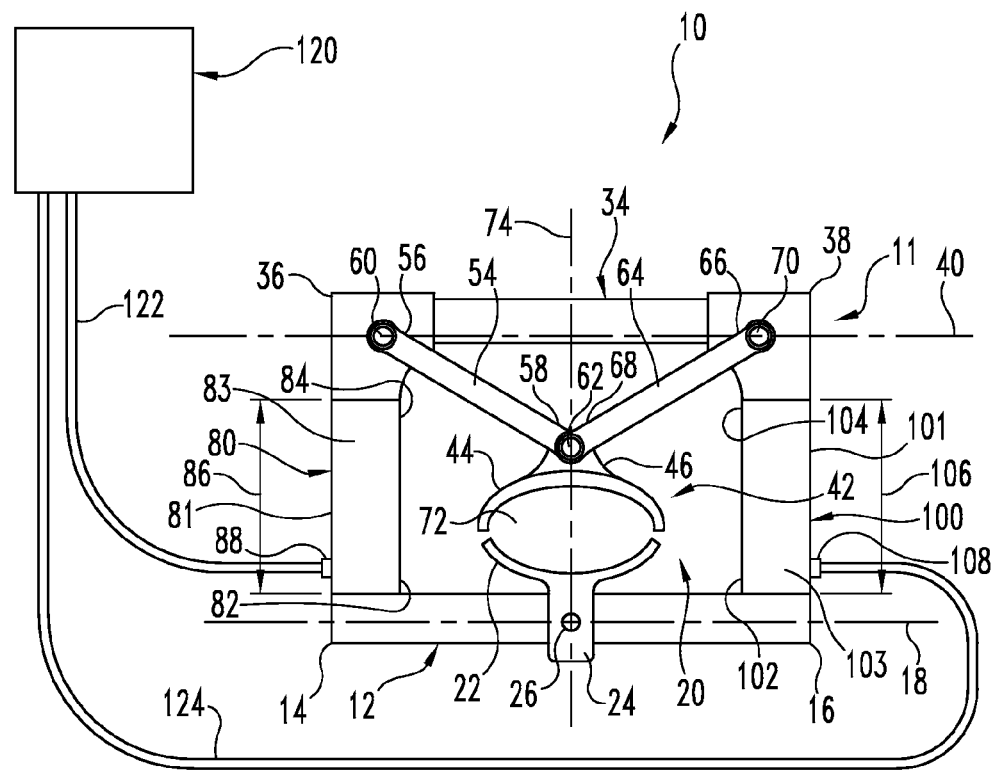
FIG. 1 is plan view of one embodiment retractor system in an insertion configuration.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion including plates, rods, and bone engaging fasteners, for example, are provided. The surgery is performed through a working channel or passageway through skin and tissue of the patient provided by a retractor system which includes a retractor. Viewing of the surgical site at the working end of the retractor can be accomplished with viewing instruments mounted on the retractor, positioned over the retractor, positioned in other portals in the body, and/or through a viewing system such as lateral fluoroscopy. The retractor is movable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

Referring now generally to FIG. 1, there is illustrated in plan view one embodiment retractor system 10 which includes a retractor 11 in an insertion configuration. Retractor 11 includes a first end portion 12 positioned opposite a second end portion 34 and a pair of actuating members 80, 100, which are positioned between first end portion 12 and second end portion 34. Actuating members 80, 100 are generally operable to move first end portion 12 and second end portion 34 relative to each other to provide a working channel 72 to a surgical site between first retractor portion 20 and second retractor portion 42. Further details regarding operation of retractor 11 are provided below.

First end portion 12 generally extends along axis 18 between first end 14 and second end 16. Positioned between first end 14 and second end 16 is a first retractor portion 20 which includes a retractor blade 22, further details of which are provided below with respect to FIG. 2. Retractor blade 22 is coupled with a coupling member 24 which is engaged with first end portion 12. It should be appreciated that blade 22 may be coupled with coupling member 24 in any suitable arrangement, including dovetail connections, fasteners, threaded coupling members, clamping members, snap rings, compression bands, straps, ball-detent mechanisms, releasably interlocking cams or tabs, welding, fusing, and/or adhering, just to name a few possibilities. In another form, blade 22 may be integrally formed with coupling member 24. Still further, retractor blade 22 may be removably coupled to coupling member 24 and an alternative retractor blade may be chosen from a plurality of retractor blades to replace retractor blade 22 to better suit a particular application in which retractor 11 is used.

Coupling member 24 is positionable along a plurality of locations on first end portion 12 between first end 14 and second end 16. It is contemplated that coupling member 24 may be of any suitable configuration for engaging with first end portion 12. In one particular form, coupling member 24 includes a pair of oppositely disposed jaws (not illustrated) which open to facilitate engagement with first end portion 12 and are closable around first end portion 12 and engageable with each other to retain coupling member 24 about first end portion 12. A locking mechanism in the form of set screw 26 is engaged with a threaded aperture in coupling member 24 to facilitate locking of coupling member 24 at a selected position between first end 14 and second end 16. Still, in another non-illustrated embodiment, coupling member 24 has a fixed position on first end portion 12. For example, coupling member 24 and first end portion 12 may be integral with one another.

Similar to first end portion 12, second end portion 34 extends along axis 40 between first end 36 and second end 38. Positioned between first end 36 and second end 38 is a second retractor portion 42 which includes a retractor blade 44, further details of which are provided below with respect to FIG. 2. Retractor blade 44 includes a coupling portion 46 in the form of a flange which is engaged with a first arm 54 and a second arm 64. First arm 54 extends between first end 56, which is coupled to second end portion 34 at first end 36 with coupling member 60, and an opposite second end 58, which is coupled to coupling portion 46 with coupling member 62. Similarly, second arm 64 includes a first end 66, which is coupled to second end portion 34 at second end 38 with coupling member 70, and an opposite second end 68, which is coupled to coupling portion 46 with coupling member 62. Arms 54, 64 extend away from second end portion 34 such that retractor portion 42 is spaced apart from second end portion 34. In this arrangement, second retractor portion 42 may be placed adjacent to first retractor portion 20 when actuating members 80, 100 are in the insertion configuration as illustrated in FIG. 1 to facilitate insertion of first and second retractor portions 20, 42 into an incision of a patient.

Coupling members 60, 70 are generally structured to engage with and couple arms 54, 64, respectively, to second end portion 34. In one form, coupling members 60, 70 utilize a threaded interconnection with second end portion 34 to secure arms 54, 64 thereto. In another form, coupling members 60, 70 may couple arms 54, 64 to second end portion through any suitable arrangement, including for example fasteners, clamping members, snap rings, compression bands, straps, ball-detent mechanisms, releasably interlocking cams or tabs, welding, fusing, and/or adhering. It is also contemplated that arms 54, 64 may be integrally formed with second end portion 34. In one particular form, coupling members 60, 70 may be structured to facilitate rotation of arms 54, 64 therearound. In another form, coupling members 60, 70 are removably engaged with second end portion 34 to facilitate removal and replacement of retractor portion 42 with an alternatively configured retractor portion. As an example, an alternatively configured retractor portion includes different length arms to alter the spacing of the retractor portion from second end portion 34. Additionally or alternatively, a retractor portion having an alternatively configured blade may replace second retractor portion 42 to better suit a particular application in which retractor 11 is used.

Similar to coupling members 60, 70, coupling member 62 is generally structured to engage with and couple arms 54, 64, to coupling portion 46. In one form, coupling member 62 utilizes a threaded interconnection with coupling portion 46 to secure arms 54, 64 thereto. In another form, coupling member 62 may couple arms 54, 64 to coupling portion 46 through any suitable arrangement, including fasteners, clamping members, snap rings, compression bands, straps, ball-detent mechanisms, releasably interlocking cams or tabs, welding, fusing, and/or adhering, just to name a few possibilities. It is also contemplated that arms 54, 64 may be integrally formed with coupling portion 46. In one form, the coupling between arms 54, 64 and coupling portion 46 is structured to facilitate rotation of retractor blade 44 about coupling member 62. Additionally, in one form coupling member 62 is removably engaged with coupling portion 46 to facilitate removal and replacement of retractor blade 44 with an alternatively configured retractor blade. In this form, it is contemplated that retractor blade 44 may be replaced individually, or in combination with one or both of arms 54, 64.

In a non-illustrated embodiment, retractor 11 is structured to facilitate alterations to the spacing of retractor portion 42 from second end portion 34. For example, each of arms 54, 64 may be telescopic or include some other extendable/contractible configuration. Additionally, retractor 11 may be configured to facilitate selective rotation or pivoting of arms 54, 64 about coupling members 60, 62, 70. As further explanation, coupling members 60, 62, 70 may utilize a threaded interconnection which can be tightened or loosened to prevent or facilitate rotation, respectively, of arms 54, 64. In this manner, when coupling members 60, 62, 70 are loosened, arms 54, 64 are free to rotate and expand or contract in response to the direction of rotation. As an example, in one direction of rotation, coupling portion 42 is moved away from second end portion 34 and the length of arms 54, 64 increases. Once a desired spacing between retractor portion 42 and second end portion 34 is achieved, coupling members 60, 62, 70 may be tightened to prevent rotation of arms 54, 64 and thereby secure the spacing between retraction portion 42 and second end portion 34 by preventing adjustments to the lengths of arms 54, 64.

Figure 2:
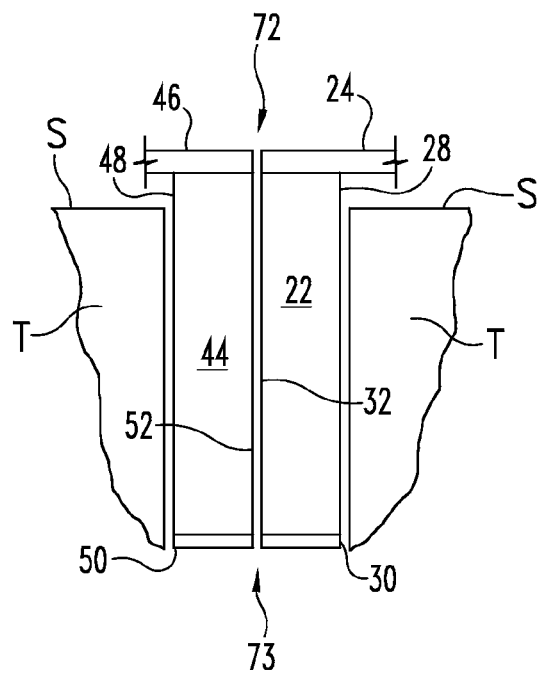
FIG. 2 is a side view of the retractor blades of the retractor system in FIG. 1.

As indicated above, further details of retractor blades 22 and 44 are illustrated in FIG. 2. Retractor blade 22 has a distal end 30 and an opposite proximal end 28. Retractor blade 44 has a distal end 50 and an opposite proximal end 48. Distal ends 30, 50 can be beveled to facilitate insertion, although non-beveled ends are also contemplated. Retractor blade 22 can be positioned adjacent to or mated with retractor blade 44 along adjacent ones of the longitudinal edges 32 of retractor blade 22 and longitudinal edges 52 of retractor blade 44. Working channel 72 is formed between first retractor blade 22 and second retractor blade 44. Working channel 72 extends between and opens at distal ends 30, 50 and proximal ends 28, 48.

Retractor blades 22, 44 are insertable through an incision in skin S and tissue T of a patient to provide working channel 72 to surgical site 73. It is contemplated that retractor blades 22, 44 are inserted through skin S and tissue T in an insertion configuration for working channel 72, such as shown in FIG. 1. In the insertion configuration, working channel 72 is substantially enclosed or circumscribed by retractor blades 22, 44. After insertion into the patient, working channel 72 can be enlarged by separating first retractor blade 22 and second retractor blade 44. Separation of retractor blades 22, 44 increases the size of working channel 72 from proximal ends 28, 48 to distal ends 30, 50.

In the insertion configuration of FIG. 1, working channel 72 is circumscribed or substantially enclosed by first retractor blade 22 and second retractor blade 44. Working channel 72 can have a size in the insertion configuration that allows passage of one or more surgical instruments and/or implants to the surgical location in the patient's body. It may be desirable during surgery to provide greater access to surgical site 73 in the patient's body beyond the locations provided through working channel 72 in its insertion configuration. First retractor blade 22 and second retractor blade 44 are movable away from one another to enlarge working channel 72. In the enlarged configuration of working channel 72, a space is formed between the adjacent longitudinal edges 32, 52 of retractor blades 22, 44. The space between the adjacent longitudinal edges 32, 52 exposes enlarged working channel 72 to skin S and tissue T of the patient between the separated first retractor blade 22 and second retractor blade 44. This exposed tissue can also be accessed by the surgeon through the enlarged working channel 72 with one or more instruments and/or implants. It is further contemplated that a shield, guard or tissue retractor could be placed in enlarged working channel 72 to maintain the exposed tissue away from the enlarged working channel 72.

Viewing instruments can be positioned in or adjacent to working channel 72 to facilitate surgeon viewing of surgical site 73. For example, an endoscopic viewing element can be mounted on the proximal end of one of retractor blades 22, 44 with a scope portion extending along working channel 72. A microscopic viewing element can be positioned over the proximal end of one of retractor blades 22, 44 for viewing surgical site 73. Other imaging techniques, such as lateral fluoroscopy, can be used alone or in combination with the endoscopic and microscopic viewing elements. It is further contemplated that other instruments can be mounted on the proximal end of one of retractor blades 22, 44, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures through retractor 11 at surgical site 73. Such viewing instruments and other instruments can be employed with working channel 72 in its initial insertion configuration and/or its enlarged configuration.

While not illustrated, it is contemplated that retractor 11 may include arrangements for aligning and releasably coupling first retractor blade 22 and second retractor blade 44 in the insertion configuration. For example, one of retractor blades 22, 44 can include one or more alignment pins which are structured to engage with a corresponding alignment aperture in the other of retractor blades 22, 44. Other arrangements are also contemplated for aligning and releasably coupling first retractor blade 22 and second retractor blade 44 to one another. Examples of such arrangements include dovetail connections, fasteners, threaded coupling members, clamping members, snap rings, compression bands, straps, ball-detent mechanisms, and releasably interlocking cams or tabs, just to name a few possibilities.

First retractor blade 22 has a perimeter length along distal end 30 which can be about the same as the perimeter length of retractor blade 22 at proximal end 28. Second retractor blade 44 includes a perimeter length along distal end 50 which can be about the same as the perimeter length of retractor blade 44 adjacent proximal end 48. Retractor blades 22, 44 can have a semi-circular cross-section, and form a generally circular cross-section for the working channel when placed adjacent one another, as shown in FIG. 1. Other cross-sectional shapes are also contemplated for first and second retractor blades 22, 44, such as, for example, any open sided polygonal shape, curved shape, or combined curved/polygonal shape. When retractor blades 22, 44 are separated from one another, working channel 72 can have a cylindrical or frusto-conical shape with, for example, a cross-section that is oval, elliptical, circular, curved, polygonal, or combined polygonal/curved in shape.

Retractor blades 22, 44 can be provided with sufficient rigidity between their distal and proximal ends to separate and maintain separation of tissue T when blades 22, 44 are initially inserted and also when tissue T is retracted by moving first retractor blade 22 and second retractor blade 44 away from one another. For example, retractor blades 22, 44 can include a thickness which provides sufficient rigidity to resist bending or bowing under the forces exerted on it by the retracted tissue T. Also, the semicircular shaped cross-section of blades 22, 44 can be configured to provide a sufficient section modulus or moment of inertia in the direction of movement of blades 22, 44 to resist bending, bowing and/or deflection forces applied during such movement.

In another non-illustrated form, retractor 11 is configured such that first and second retractor blades 22, 44 can be pivoted or rotated toward one another about their proximal ends to provide working channel 72 with a tapered configuration that reduces in size from the distal ends of retractor blades 22, 44 through skin S to the proximal ends of retractor blades 22, 44. A tapered working channel provides the surgeon greater access and increased visualization of surgical site 73 while minimizing tissue retraction. The tapered working channel 72 also allows greater angulation of instruments and implants placed through working channel 72, more selection in positioning of instruments and implants within working channel 72, and the ability to position instruments and implants adjacent the inner wall surfaces of the separated first and second retractor blades 22, 44, increasing the room available at surgical site 73 for multiple instruments and for orienting implants.

One particular application for retractor 11 is in spinal surgery. It is contemplated that, after insertion of retractor blades 22, 44, they are separated predominantly in one direction to retract muscle and tissue along axis 74 which extends between first and second retractor portions 20, 42. For example, first and second retractor blades 22, 44 of retractor 11 can be primarily or predominantly separable in the direction of the spinal column axis. The muscle tissue adjacent the spine has a fiber orientation that extends generally in the direction of the spinal column axis. The separation of retractor blades 22, 44 of retractor 11 can also separate the muscle tissue along the fibers, thus the amount of separation and the resultant tearing and trauma to the muscle tissue can be minimized. It is also contemplated in other techniques employing retractor 11 that working channel 72 can be enlarged primarily in a direction other than along the spinal column axis or in areas other than spine.

In one example, a method for positioning retractor blades 22, 44 through skin S and tissue T includes making an incision through skin S adjacent the location of a surgical site. For example, in spinal surgery, the incision can be made at a vertebral level at a location that provides access to the disc space between adjacent vertebrae or to one or more vertebra through a desired approach. Prior to insertion of retractor blades 22, 44, skin S and tissue T can be sequentially dilated via a dilation instrument set (not illustrated) which can include guidewires and/or one or more tissue dilators of increasing size. The tissue dilators are inserted one over another to form a pathway through skin S and tissue T to the surgical site in the patient. In such procedures, retractor blades 22, 44 are positioned over the last inserted dilator to form the pathway in the skin S and tissue T. Working channel 72 through retractor blades 22, 44 provides access to surgical site 73 at the distal ends of retractor blades 22, 44 when the guidewires and dilators, if used, are removed therefrom.

Figure 3:
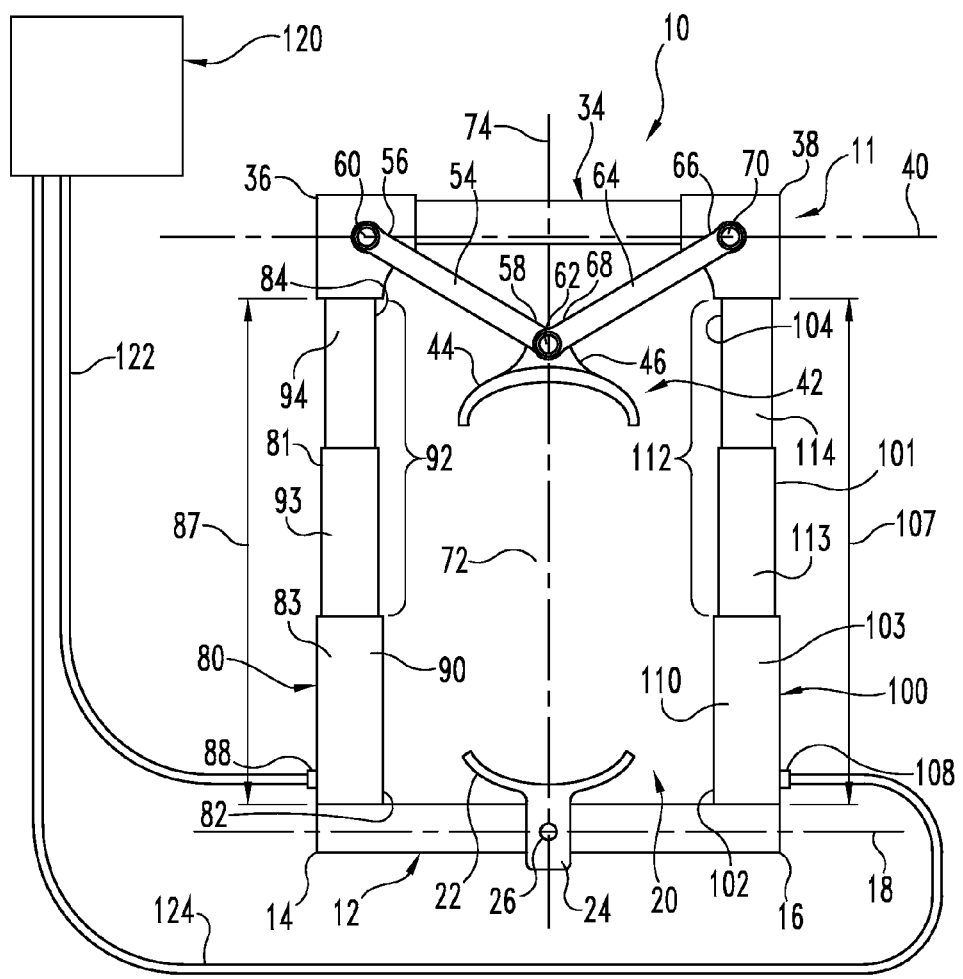
FIG. 3 is a plan view of the retractor system in FIG. 1 in an expanded configuration.

For the entire surgery or for certain procedures during the surgery, it may be desired by the surgeon to increase the size of working channel 72 to facilitate access to surgical site 73. First and second retractor blades 22, 44 of retractor 11 can be separated from their insertion configuration to a separated configuration in which working channel 72 is enlarged, as shown in FIG. 3. In the enlarged configuration, first retractor blade 22 and second retractor blade 44 can be moved laterally away from one another by actuating members 80, 100, further details of which are provided below. Adjacent ones of the edges 32, 52 are separated and working channel 72 is exposed to skin S and tissue T along axis 74 while first and second retractor blades 22, 44 hold tissue out of the operative field.

With further reference to actuating members 80, 100, general reference to FIGS. 1 and 3 is made. In the illustrated embodiment of retractor system 10, actuating members 80, 100 are in the form of cylinder mechanisms 81, 101, respectively. However, other configurations for actuating members 80, 100 are contemplated, as discussed further below. Cylinder mechanism 81 includes a body 83 which extends between a first end 82 and an opposite second end 84. Ends 82, 84 are coupled with respective ones of first end portion 12 and second end portion 34 in any suitable arrangement, including dovetail connections, fasteners, threaded coupling members, clamping members, snap rings, compression bands, straps, ball-detent mechanisms, releasably interlocking cams or tabs, welding, fusing, and/or adhering, just to name a few possibilities. As illustrated by arrow 86, body 83 has an initial length between ends 82, 84 when retractor 11 is in the insertion configuration. Cylinder mechanism 81 also includes a connector 88 which connects pathway 122 to cylinder mechanism 81. The opposite end of pathway 122 is connected with a controller 120 such that cylinder mechanism 81 and controller 120 are in communication with one another.

Cylinder mechanism 101 includes a body 103 which extends between a first end 102 and an opposite second end 104. Ends 102, 104 are coupled with respective ones of first end portion 12 and second end portion 34 in any suitable arrangement, including dovetail connections, fasteners, threaded coupling members, clamping members, snap rings, compression bands, straps, ball-detent mechanisms, releasably interlocking cams or tabs, welding, fusing, and/or adhering, just to name a few possibilities. As illustrated by arrow 106, body 103 has an initial length between ends 102, 104 when retractor 11 is in the insertion configuration. Cylinder mechanism 101 also includes a connector 108 which connects pathway 124 to cylinder mechanism 101. The opposite end of pathway 124 is connected with controller 120 such that cylinder mechanism 101 and controller 120 are in communication with one another.

Figure 4:
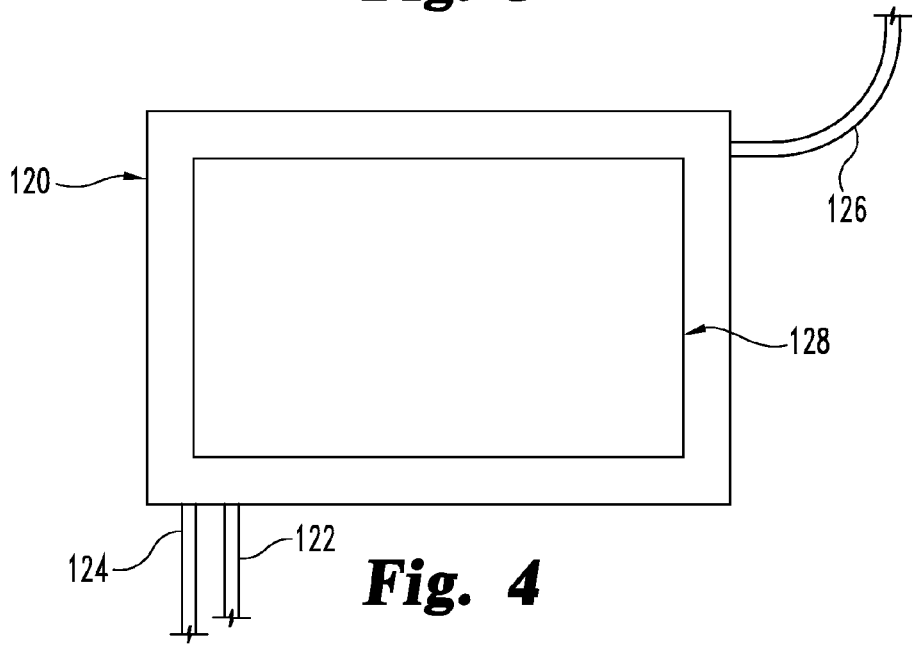
FIG. 4 is a plan view of one embodiment controller unit illustrated in FIG. 1.

As illustrated in plan view in FIG. 4, controller 120 includes a user interface 128. Interface 128 may include a touch-screen, switches, buttons, levers, keypad, keyboard and/or mouse, just to name a few possibilities, with which a user can provide an actuation command to controller 120. In response to the actuation command, the length of actuators 80, 100 is adjustable to provide a desired separation between retractor portions 20, 42. For example, in FIG. 3, the length of actuators 80, 100 between opposite first and second ends has been increased, as indicated by arrows 87, 107, in response to an actuation command to separate first and second retractor portions 20, 42 along axis 74 and increase the size of working channel 72. Similarly, the length of actuating members 80, 100 may be decreased between the opposite first and second ends in response to an actuation command to move retractor portions closer together and decrease the size of working channel 72. It should be appreciated that interface 128 and controller 120 may facilitate actuation of actuating members 80, 100 either alone or in combination with one another.

Controller 120 operates in accordance with operating logic to actuate actuating members 80, 100 in accordance with an actuation command. Controller 120 is comprised of one or more components that may be configured as a single unit, or distributed among two or more units. Such components may be of a solid state, electromagnetic, optical, and/or different variety as would occur to those skilled in the art. Controller 120 may include analog circuitry, digital circuitry, and/or a hybrid combination of both of these types. In one form, controller 120 is of the programmable variety that executes algorithms and processes data in accordance with its operating logic being defined by programming instructions (such as software or firmware). Alternatively or additionally, the operating logic for controller 120 is at least partially defined by hardwired logic or other hardware. As illustrated in FIG. 4, controller 120 includes power supply 126 which may supply power to controller 120 from an external source, such as an electrical socket. In another non-illustrated form, a power supply is located within internal controller 120 and may be provided for example, in the form of one or more electrochemical cells or battery of such cells. It should be appreciated that controller 120 may be modified for use with a DC power source or an AC power source and that the modification of components may be dependent upon the availability of one or more forms of the power source. Additional variations to controller 120 will become apparent with respect to various configurations of actuating member 80, 100.

With reference again to FIG. 3, cylinder mechanism 81 includes a base 90 and a piston assembly 92 which includes an intermediate portion 93 and a terminal portion 94. Base 90 includes one or more internal chambers which include a fluid, or to which a fluid may be supplied. As the pressure of the fluid in the internal chamber(s) increases beyond a threshold level, a force is imparted on piston assembly 92 and one or both of portions 93, 94 is extended from base 90. While piston assembly 92 has been illustrated with portions 93, 94, it should be appreciated that it may include one or more portions in addition to or in lieu of those illustrated. Additionally, it is contemplated that cylinder mechanism 81 can be a single acting or double acting cylinder. In one particular form, cylinder mechanism 81 is a double acting cylinder and both extension and retraction of piston assembly 92 are controlled by the pressure of a fluid, as would be appreciated by those skilled in the art.

Cylinder mechanism 101 includes a base 110 and a piston assembly 112 which includes an intermediate portion 113 and a terminal portion 114. Base 110 includes one or more internal chambers which include a fluid, or to which a fluid may be supplied. As the pressure of the fluid in the internal chamber(s) increases beyond a threshold level, a force is imparted on piston assembly 112 and one or both of portions 113, 114 is extended from base 110. While piston assembly 112 has been illustrated with portions 113, 114, it should be appreciated that it may include one or more portions in addition to or in lieu of those illustrated. Additionally, it is contemplated that cylinder mechanism 101 can be a single acting or double acting cylinder. In one particular form, cylinder mechanism 101 is a double acting cylinder and both extension and retraction of piston assembly 112 are controlled by the pressure of a fluid, as would be appreciated by those skilled in the art.

When piston assemblies 92, 112 are extended, retractor portions 20, 42 are separated from one another as illustrated in FIG. 3 to increase the size of working channel 72. Similarly, upon retraction of piston assemblies 92, 112, retractor portions 20, 42 are positioned adjacent one another in the insertion configuration illustrated in FIG. 1. It should also be appreciated that movement of retractor portions 20, 42 to any position between the insertion configuration of FIG. 1 and the extended configuration of FIG. 3 is contemplated by the subject application.

In one particular embodiment, cylinder mechanisms 81, 101 are in the form of pneumatic cylinders. In this embodiment, controller 120 controls a flow of compressed air between controller 120 and mechanisms 81, 101 through pathways 122, 124. Controller 120 can be coupled with a source of compressed air or can include a compressor for generating compressed air. In response to an actuation command provided by a user at interface 128, controller 120 may actuate one or more valves to regulate the flow of compressed gas to one or both of cylinder mechanisms 81, 101 and thereby adjust the pressure of compressed air in the internal chamber(s). In response to the adjustment of pressure, piston assemblies 92, 112 are extended or retracted from bases 90, 110. It is contemplated that the valve(s) may be positioned at controller 120 or at cylinder mechanisms 81, 101. When the valves are positioned at controller 120, pathways 122, 124 are in the form of hollow tubing. In one variant of this form, it is contemplated that the tubing of pathways 122, 124 may be coaxial to provide compressed air to mechanisms 81, 101 and also return air from mechanisms 81, 101. Alternatively, one or more additional pathways may be provided between controller 120 and mechanisms 81, 101 to facilitate the supply and return of compressed air. In another form where the valves are positioned at mechanisms 81, 101, pathways 122, 124 may provide a control signal to the valves in addition to providing and returning compressed air. As an example, the valves may include an electromechanical configuration structured to operate in response to an electrical signal. Upon receiving an actuation command, controller 120 sends an electrical signal to the valves to actuate mechanisms 81, 101 in accordance with the actuation commands.

In another embodiment, controller 120 may be configured to regulate the flow of a hydraulic fluid to mechanisms 81, 101. Examples of hydraulic fluids include water, water-based mixtures, oils, mineral oil, synthetic compounds and/or mixtures thereof, just to name a few possibilities. Controller 120 is coupled with a source of hydraulic fluid and includes a combination of one or more pumps and valves to regulate the flow of hydraulic fluid between controller 120 and cylinder mechanisms 81, 101 in response to a user actuation command provided at interface 128. It is contemplated that pathways 122, 124 may be provided as coaxial tubing to facilitate both the supply and return of hydraulic fluid to cylinder mechanisms 81, 101. As discussed above, piston assemblies 92, 112 extend and retract from bases 90, 110 in response to the pressure of the hydraulic fluid. Similarly, the pressure of the hydraulic fluid is controlled by controller 120 in response to actuation commands.

In still another embodiment, the internal chambers of bases 90, 110 include a magnetorheological fluid surrounded by one or more electromagnetic elements, which are electrically coupled with controller 120 through pathways 122, 124. The magnetorheological fluid includes micrometer-sized magnetic particles which are suspended randomly throughout the fluid in the absence of a magnetic field. However, when a magnetic field is applied to the magnetorheological fluid, the magnetic particles align themselves along the direction of magnetic flux of the magnetic field. When a user provides an actuation command at interface 128, controller 120 processes the actuation command and provides an electrical current through pathways 122, 124 to the electromagnetic elements of cylinder mechanisms 81, 101. Controller 120 varies the strength of the electrical current to correspond to the amount of movement between retractor portions 20, 42 associated with the actuation command; i.e., the force of the electric current is related to the amount of movement to be accomplished by the actuation command. Generally, as the force of the electrical current increases, the electromagnet elements create a stronger magnetic field. As the force of the magnetic field increases, the viscosity of the magnetorheological fluid is increased until it has a solid or "solid-like" consistency. As the viscosity increases, a force is exerted on piston assemblies 92, 112 and one or more of portions 93, 94 and 113, 114 is extended. Similarly, when the force of the electrical current is reduced, the force of the magnetic field and the viscosity of the magnetorheological fluid are also reduced and the magnetorheological fluid moves away from the solid or "solid-like" consistency. In this arrangement, piston assemblies 92, 112 are forced to return toward bases 90, 110 by the pressure of the surrounding tissue and skin. Alternatively, cylinder mechanisms 81, 101 may include one or more biasing members to facilitate retraction of piston assemblies 92, 112 when the force of the electrical current is reduced or eliminated.

Figure 5:
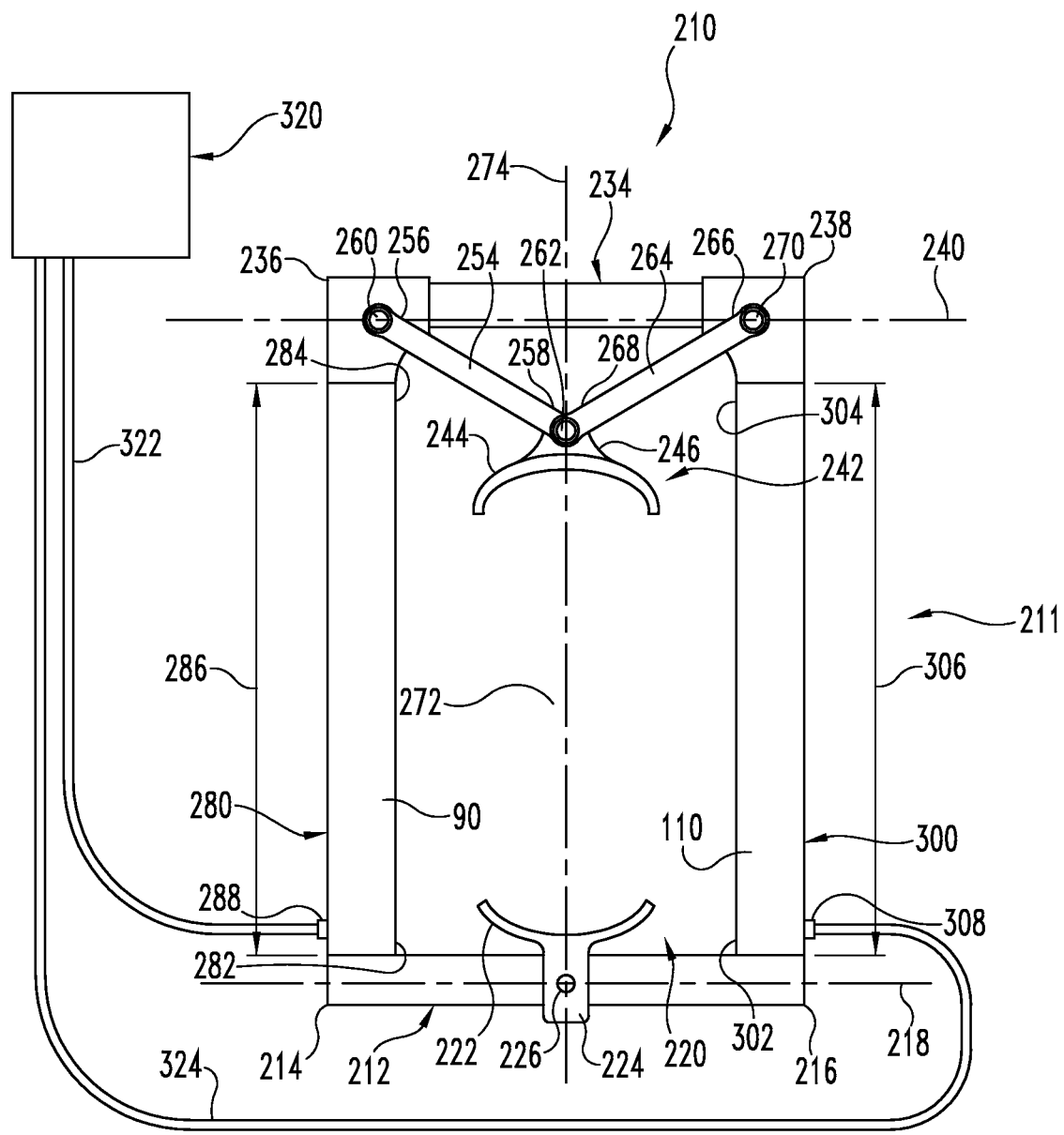
FIG. 5 is a plan view of an alternative embodiment retractor system.

In FIG. 5, there is shown in plan view an alternative embodiment retractor system 210 where retractor 211 is in an expanded configuration and like numerals refer to like features previously described. While not illustrated, it should be appreciated that retractor 211 also includes an insertion configuration similar to that illustrated in FIG. 1, where retractor portions 220, 242 are positioned adjacent one another. Additionally, it is contemplated that system 210 may be used as described above with respect to system 10. Retractor 211 of system 210 includes a pair of oppositely disposed actuating members 280, 300 which are defined by an electroactive polymer material. As way of background, electroactive polymers are polymers that respond to electrical stimulation with a shape or size change. Each of actuating members 280, 300 includes an electrode configuration (not shown) structured to provide electrical stimulation to the electroactive polymer material. The electrode configurations are electrically coupled to controller 320 via pathways 322, 324. In response to an actuation command provided to controller 320 by a user, controller 320 provides an electrical current to the electrode configurations. It should be appreciated that the electrical current may correspond to the amount of actuation associated with the actuation command. When the electrical current provided by controller 320 is received by the electrode configurations, electrical stimulation of the electroactive materials is performed to provide actuation of actuating members 280, 300. For example, the electrical stimulation increases the length (indicated by arrows 286, 306) of actuating members 280, 300 and separates first and second retractor portions 220, 242 as illustrated in FIG. 5. During a surgical procedure, controller 320 may continually provide electrical current to actuating members 280, 300 to retain working channel 272 in its expanded configuration. Upon completion of the surgical procedure, or before if desired, the electrical current is terminated and the electroactive material of actuating members 280, 300 retracts, thereby positioning retractor 211 toward its insertion configuration where retractor portions 220, 242 are positioned adjacent one another. While not intending to be limited to any particular configuration, further details of one electroactive polymer actuator are provided in *Dielectric Elastomer Actuators in the Development of a Mechantronic Muscle.* O'Halloran et al., NUI, GALWAY FACULTY OF ENGINEERING RESEARCH DAY 2004. Details of another electroactive polymer actuator may be found in *Low-mass Muscle Actuators Using Electroactive Polymers (EAP)*, Cohen et al., Proceedings of SPIE's 5$^{th}$ Annual International Symposium on Smart Structures and Materials, Mar. 1-5, 1998. Paper No. 3324-32.

Another embodiment retractor system 410 is illustrated in FIGS. 6-9. System 410 includes a retractor 420 which includes a first retractor portion 422 and a second retractor portion 442. First portion 422 includes a body 423 extending between a distal end 424 and an opposite proximal end 426. Second portion 442 includes a body 443 extending between a distal end 444 and an opposite proximal end 446. Distal ends 424, 444 can be beveled or distally tapered to facilitate insertion, although non-beveled ends are also contemplated. First portion 422 can be positioned adjacent to or mated with second portion 442 along adjacent ones of the longitudinal edges 425, 427 of first portion 422 and longitudinal edges 445, 447 of second portion 442. It is further contemplated that the longitudinal edges can be spaced from one another in the insertion configuration. A working channel 450 is formed between first portion 422 and second portion 442. Working channel 450 extends between and opens at distal ends 424, 444 and proximal ends 426, 446.

Figure 6:
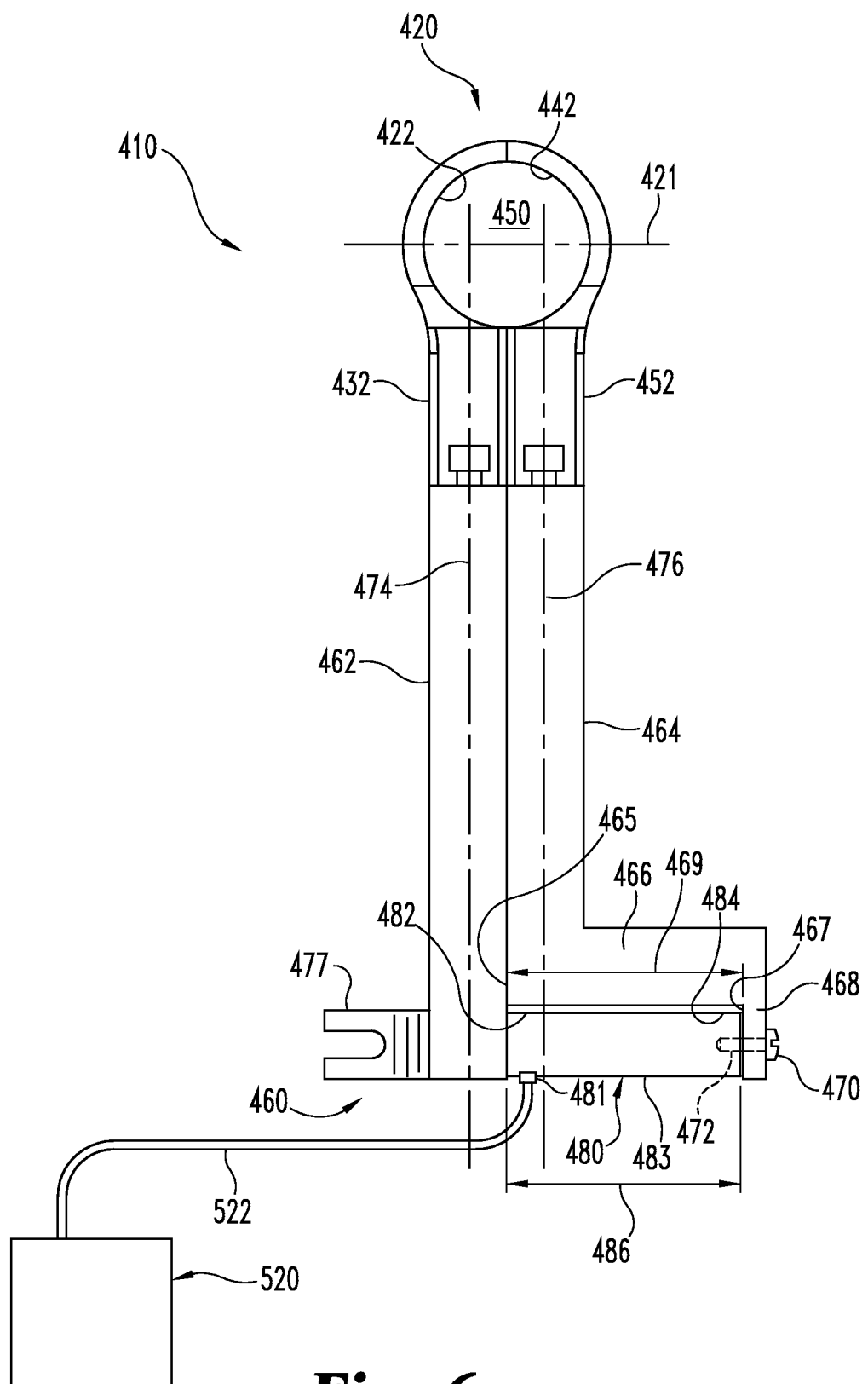
FIG. 6 is a plan view of another alternative embodiment retractor system.
Figure 7:
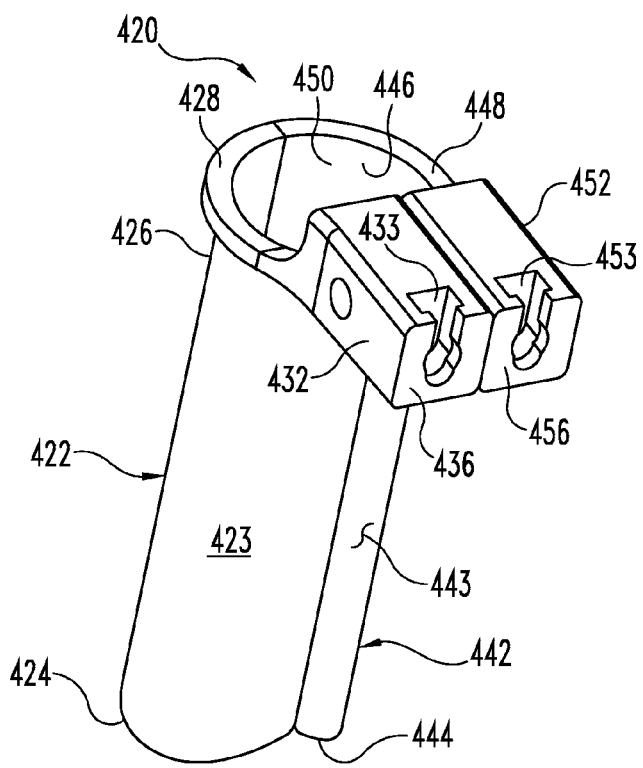
FIG. 7 is a perspective view of a pair of retractor portions of the retractor system in FIG. 6.
Figure 8:
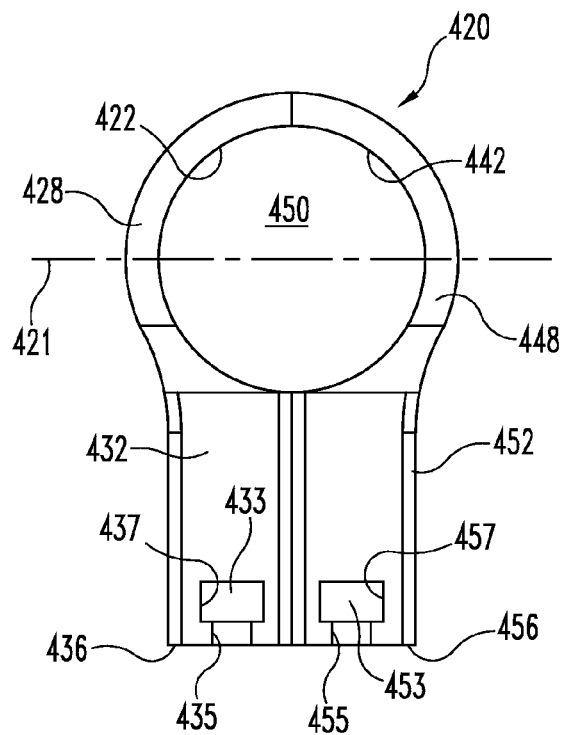
FIG. 8 is a plan view of the retractor portions of FIG. 7.

Retractor 420 is insertable through skin and tissue of a patient to provide working channel 450 to a surgical site. It is contemplated that retractor 420 is inserted through the skin and tissue in an insertion configuration for working channel 450, such as shown in FIGS. 6-8. In the insertion configuration, working channel 450 is substantially enclosed or circumscribed by first portion 422 and second portion 442. After insertion into the patient, working channel 450 can be enlarged by separating first portion 422 and second portion 442 away from one another along an axis 421 extending therebetween. Separation of first and second portions 422, 442 increases the size of working channel 450 from proximal ends 426, 446 to distal ends 424, 444.

In the insertion configuration of FIGS. 6-8, working channel 450 is circumscribed or substantially enclosed by first portion 422 and second portion 442. Bodies 423 and 443 can be configured as discussed above with respect to retractor blades 22, 44 of retractor 11. Working channel 450 can have a size in the insertion configuration that allows passage of one or more surgical instruments and/or implants to the surgical location in the patient's body, although smaller sizes are also contemplated. It may be desirable during surgery to provide greater access to the location in the patient's body beyond the locations provided through working channel 450 in its insertion configuration. Accordingly, first portion 422 and second portion 442 are movable away from one another along axis 421 to enlarge working channel 450.

First portion 422 includes body 423 with a semi-cylindrical shape extending between distal end 424 and proximal end 426. A collar 428 extends about proximal end 426, and forms a lip extending about the outer surface of body 423. Second portion 442 includes body 443 having a semi-cylindrical shape extending between distal end 444 and proximal end 446. A collar 448 extends about proximal end 446 of second portion 442, and defines a lip extending about the outer surface of body 443. It is further contemplated that first and second portions 422, 442 can be provided with or without a collar and/or a lip. First and second portions 422, 442 can also be provided with bracket members for engagement with an external arm that supports retractor 420 while positioned in the patient.

Extending from collar 428 of first portion 422 is a first engagement member 432 having a head portion 436 forming a recess 433 therein. Extending from collar 448 of second portion 442 is a second engagement member 452 having a head portion 456 forming a recess 453 therein. Engagement members 432, 452 can be integrally formed with or removably engaged to the respective collars 428, 448. As discussed further below, an actuating assembly for separating first portion 422 and second portion 442 can be non-releasably or releasably engaged to engagement members 432, 452 for application of a separation force to enlarge working channel 450 by separating first portion 422 and second portion 442. Such an actuating assembly could also be releasably or non-releasably engaged to first portion 422 and second portion 442. Engagement members 432, 452 extend laterally from portions 422, 442 to allow engagement of the actuating assembly to engagement members 432, 452 without obstructing working channel 450 with the actuating assembly. Such an actuating assembly could also maintain first portion 422 and second portion 442 in the initial insertion configuration during and after insertion. The actuating assembly can also maintain the enlarged configuration of working channel 450 in situ.

Recesses 433, 453 are adapted to receive engagement assemblies of the actuating assembly engageable to portions 422, 442. In the illustrated embodiments, engagement members 432, 452 extend laterally from and project proximally above the respective collars 428, 448. Engagement members 432, 452 extend alongside one another and abut one another when portions 422, 442 are in their insertion configuration. Other configurations for the engagement members are also contemplated, including engagement members that are non-linear, that extend in directions away from one another when portions 422, 424 are in their insertion configuration, and engagement members that do not abut one another in the insertion configuration.

Recesses 433, 453 open laterally to receive respective ones of the engagement assemblies of the actuating assembly. Recess 433 includes a keyway opening 435 and a receptacle 437 in communication with opening 435. Receptacle 437 is enlarged relative to opening 435, and is shaped to receive a portion of the engagement assembly of the actuating assembly positioned therein. Similarly, recess 453 includes a keyway opening 455 and a receptacle 457 in communication with opening 455. Receptacle 457 is enlarged relative to opening 455, and is shaped to receive a portion of the engagement assembly of the actuating assembly positioned therein. Openings 435, 455 and receptacles 437, 457 are open along the proximal sides of the respective engagement members 432, 452 to facilitate placement of the actuating assembly engagement assemblies therein. Other configurations for the recess 433, 453 are also contemplated, including recesses that are enclosed, uniform, or any other suitable configuration to receive at least a portion of an engagement assembly. Still other embodiments contemplate that engagement members 432, 452 do not include recesses, but rather are shaped for receipt in or otherwise engage the respective engagement assembly of the actuating assembly. In yet another embodiment, it is contemplated that engagement members 432, 452 and the engagement assemblies of the actuating assembly are integrally formed.

Figure 9:
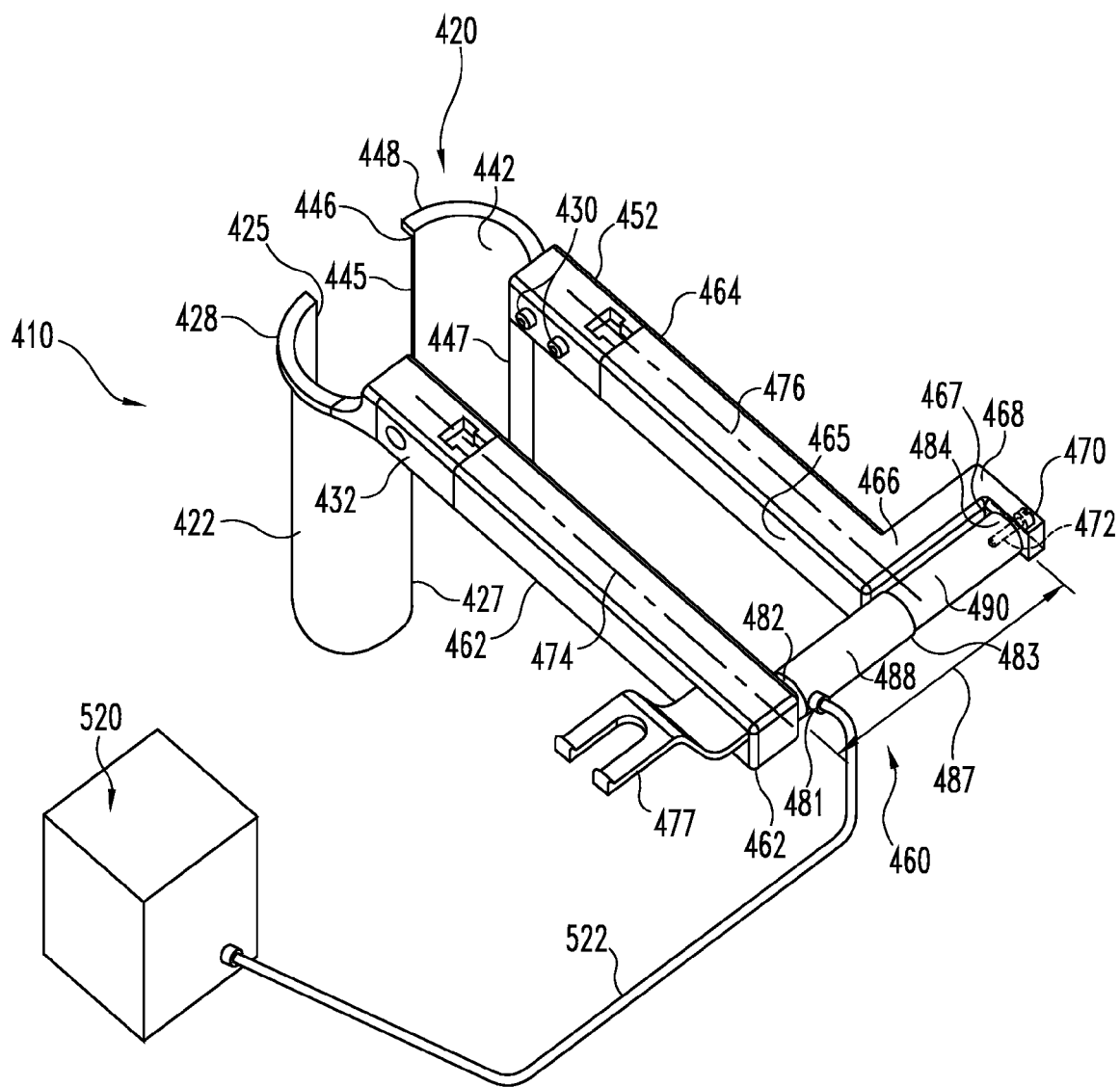
FIG. 9 is a perspective view of the retractor system of FIG. 6 with the retractor portions separated.

As shown in FIG. 9, alignment members 430 can be provided along one side of one of the engagement members 432, 452 (engagement member 452 in the illustrated embodiment). In the illustrated embodiment, alignment members 430 are rounded protrusions which are received in holes provided in the adjacent side of the other engagement member 432, 452 when engagement members 432, 452 are positioned adjacent one another. Alignment members 430 maintain first portion 422 and second portion 442 in longitudinal alignment with one another during and after insertion. Other embodiments contemplate other arrangements for aligning and/or releasably coupling first portion 422 and second portion 442 to one another. Examples of such arrangements include dovetail connections, fasteners, threaded coupling members, clamping members, snap rings, compression bands, straps, ball-detent mechanisms, and releasably interlocking cams or tabs, for example.

Referring to FIGS. 6 and 9, there is shown an actuating assembly 460 including an actuating member 480 which is operable to move first and second portions 422, 442 away from one another to enlarge working channel 450. It is contemplated that actuating assembly 460 is operable to linearly move first and second retractor portions away from one another along axis 421. Actuating member 480 can be selectively actuated by the surgeon during the surgical procedure to control the size of working channel 450 and provide the tissue retraction desired for conducting the surgical procedure through working channel 450. Enlargement of working channel 450 can further retract tissue away from the surgical site distal of the distal ends of retractor portions 422, 442 to provide greater access to tissue, bony structures, and other anatomical spaces located distally of retractor 420.

Actuating assembly 460 includes a first connection assembly 462 movably coupled with a second connection assembly 464. First connection assembly 462 extends along axis 474 and is further coupled to first portion 422, and second connection assembly 464 extends along axis 476 and is coupled to second portion 442. First and second connection assemblies 462, 464 extend away from first and second portions 422, 442 and away from the proximal end opening of working channel 450 to facilitate access to working channel 450 during the surgical procedure. First and second connection assemblies 462, 464 are operable to move first and second portions 422, 442 toward and away from one another to separate tissue upon actuation of actuating member 480. While not illustrated, it is contemplated that first and second connection assemblies 462, 464 may be structured to facilitate rotation of first and second portions 422, 442 about their proximal ends to move their distal ends away from one another. Additionally, first connection assembly 462 includes a bracket member 477 which is engageable by a flexible arm mounted to a surgical table, for example.

Actuating member 480 is in the form of a cylinder mechanism 483 which extends between a first end 482 and a second end 484 and includes a length in the insertion configuration illustrated in FIG. 6 which is represented by arrow 486. Cylinder mechanism 483 includes a connector 481 which connects pathway 522 to cylinder mechanism 483. The opposite end of pathway 522 is connected with a controller 520 such that cylinder mechanism 483 and controller 520 are in communication with one another. First end 482 of cylinder mechanism 483 is coupled with first connection assembly 462 while second end 484 is coupled with second connection assembly 464. More particularly, second connection assembly 464 includes an offset end portion 466 which terminates in a flange 468. Offset end portion 466 includes a length, indicated by arrow 469, between surface 465 and surface 467 which substantially corresponds to the length, indicated by arrow 486, of cylinder mechanism 483 in the insertion configuration illustrated in FIG. 6. Flange 468 includes an aperture through which coupling member 470 extends to engage with second end 484 of cylinder mechanism 483. In the illustrated form, coupling member 470 is in the form of a screw or bolt which includes a threaded stem 472 that engages with a corresponding threaded structure (not shown) of cylinder mechanism 483. Other arrangements for coupling flange 468 to cylinder mechanism 493 are contemplated, including for example, dovetail connections, fasteners, clamping members, snap rings, compression bands, straps, ball-detent mechanisms, releasably interlocking cams or tabs, welding, fusing, and/or adhering. Such arrangements may also be suitable for coupling first end 482 of cylinder mechanism 483 with first connection assembly 462.

Cylinder mechanism 483 includes a base 488 and a piston assembly 490. It should be appreciated that cylinder mechanism 483 includes features similar to those discussed above with respect to cylinder mechanisms 81, 101 and may be a pneumatic cylinder, hydraulic cylinder or a magnetorheological fluid actuator, as discussed above with respect to retractor system 10. Furthermore, controller 520 may be configured similar to any of the embodiments described above with respect to controller 120 of retractor system 10. Thus, in response to an actuation command provided to controller 520 by a user, the length of cylinder mechanism 483 is adjusted. For example, piston assembly 490 can be extended from base 488 to increase the length (indicated by arrow 487 in FIG. 9) of cylinder mechanism 483 and the size of working channel 450. In another embodiment, it is contemplated that retractor system 410 utilizes an electroactive polymer actuating member such as that described above with respect to system 210.

In one embodiment, a retractor system for percutaneous surgery in a patient includes a first retractor portion including a proximal end and a distal end positionable in an incision. A second retractor portion includes a proximal end and a distal end positionable in the incision opposite the first retractor portion. The first and second retractor portions define an axis extending therebetween. The system also includes an actuating member coupled with the proximal ends of the first and second retractor portions. The actuating member includes a length between opposite first and seconds ends which is adjustable in response to actuation of the actuating member. A controller is provided in communication with the actuating member and includes a user interface for receiving actuation commands from the user. In response to actuation commands, the actuating member is operable to position the first and second retractor portions relative to each other along the axis.

In another embodiment, a method for retracting tissue for percutaneous access to a surgical site in a patient is provided. The method includes providing a retractor system which includes a first retractor portion including a proximal end and a distal end positionable in an incision. A second retractor portion includes a proximal end and a distal end positionable in the incision opposite the first retractor portion with the first and second retractor portions defining an axis extending therebetween. The system also includes an actuating member coupled with the proximal ends of the first and second retractor portions which includes a length between opposite first and seconds ends. A controller which is remotely positioned from and in communication with the actuating member is also included in the system. The method also includes providing an actuation command at the controller, and in response to the actuation command, positioning the first and second retractor portions relative to each other along the axis.

In still another embodiment, a retractor system for percutaneous surgery in a patient includes a first end portion extending along a first axis between first and second ends and including a first retractor blade positioned between the first and second ends. Similarly, a second end portion extends along a second axis between first and second ends and includes a second retractor blade positioned between the first and seconds. A third axis is defined by and extends between the first and second retractor blades. The retractor system also includes first and second actuating members coupled between the first and second end portions. The first and second actuating members are adjustable in response to actuation of the actuating members to position the first and second retractor portions relative to each other along said axis.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A method for retracting tissue for percutaneous access to a surgical site in a patient, comprising:
  providing a retractor system including:
    a first retractor portion including a first retractor blade having a concave inner surface positionable in an incision;
    a second retractor portion including a first retractor blade having a concave inner surface positionable in the incision opposite the first retractor portion, said first and second retractor blades defining an axis extending therebetween;
    first and second actuating members coupled with the proximal ends of said first and second retractor portions in offset relation to and on opposite sides of said axis, wherein said first and second actuating members each include a length between opposite first and seconds ends, each of said lengths being adjustable in response to actuation of said first and second actuating members wherein at least one of said first and second actuating members is a pneumatic cylinder mechanism including a piston and a chamber, said piston being structured to move in response to pressure of a fluid; and
    a controller remotely positioned from, and in communication with, said first and second actuating members;
  providing an actuation command at said controller;
  regulating air pressure in response to actuation commands in said chamber; and
  in response to the actuation command, adjusting a length of said first and second actuating members alone or in combination to position said first and second retractor portions relative to each other along said axis.

2. A retractor system for percutaneous surgery in a patient, comprising:
  a first end portion extending along a first axis between first and second ends and including a first retractor blade extending from a first retractor portion positioned between said first and second ends;
  a second end portion extending along a second axis between first and second ends and including a second retractor blade positioned between said first and second end portions, said second retractor blade being coupled with a pair of arms extending from a section of said second end portion that extends parallel to said second axis such that said arms extend into a space between said first and second end portions, said first and second retractor blades defining a third axis extending therebetween and a second retractor portion is adjustably coupled to said second end portion to adjust a spacing between said second retractor portion and said second end portion along said third axis; and
  a first actuating member coupled between said first end portion and said second end portion;
  a second actuating member coupled between said first end portion and said second end portion; and wherein said first and second actuating members are adjustable in response to actuation of said actuating members to position said first and second retractor blades relative to each other;
  wherein at least one of said first and second actuating members is a pneumatic cylinder mechanism including a piston and a chamber, said piston being structured to move in response to pressure of a fluid.

3. The system of claim 2, wherein said pair of arms comprises a first arm and a second arm, said first arm extending at a first angle relative to said second axis and said second arm extending at a second angle relative to said second axis, said second angle being an inverse angle of said first angle.

4. The system of claim 2, wherein one of said pair of arms extends from the first end of said second end portion to an end of said one arm and the other of said pair of arms extends from the second end of said second end portion to an end of said other arm, and said second retractor blade is rotatably coupled to said ends of said first and second arms in said space.

5. The system of claim 2, wherein said second retractor blade is spaced apart from said second end portion.

6. The system of claim 5, wherein said first retractor blade is positioned adjacent to said first end portion.

7. The system of claim 2, further comprising a controller remote from and in communication with said first and second actuating members, said controller including a user interface for receiving actuation commands from the user and wherein said first and second actuating members are operable to respond to the actuation commands.

8. The system of claim 7, wherein each of said first and second actuating members includes a length between opposite first and second ends, said length being adjustable in response to actuation of the respective actuating member.

9. The method of claim 1, wherein said inner surfaces face one another.

10. The method of claim 1, wherein positioning said first and second retractor portions relative to each other comprises moving said first and second retractor blades from a first configuration in which said first and second retractor blades engage one another to a second configuration in which said first and second retractor blades are spaced apart from one another.

11. The method of claim 1, wherein said first and second retractor blades are inserted through an incision using a posterior approach.

12. The method of claim 1, wherein said first and second retractor blades are inserted through an incision such that inner surfaces of said first and second retractor blades define a working channel that provides access to a portion of the patient's spine.

13. The system of claim 2, wherein said arms are directly coupled to said second end portion by coupling members that threadingly engage said second end portion.

14. The system of claim 13, wherein said coupling members are movable from a first orientation in which said coupling members are tightened and said arms are free to rotate about axes defined by said coupling members and a second orientation in which said coupling members are tightened and said arms are prevented from rotating about said axes defined by said coupling members.

15. The system of claim 2, wherein said arms are each telescopic.

* * * * *